(12) United States Patent
Bordayo et al.

(10) Patent No.: US 11,806,028 B1
(45) Date of Patent: Nov. 7, 2023

(54) SURGICAL GUIDES AND PROCESSES FOR PRODUCING AND USING THE SAME

(71) Applicant: restor3d, Inc., Durham, NC (US)

(72) Inventors: Joel Bordayo, Durham, NC (US);
Brian Garvey, Raleigh, NC (US);
Dhwanit Shashi Vispute, Durham, NC (US); Deepak Padmanabhan, Durham, NC (US)

(73) Assignee: RESTOR3D, INC., Durham, NC (US)

(*) Notice: Subject to any disclaimer, the term of this patent is extended or adjusted under 35 U.S.C. 154(b) by 0 days.

(21) Appl. No.: 18/148,796

(22) Filed: Dec. 30, 2022

Related U.S. Application Data

(60) Provisional application No. 63/413,189, filed on Oct. 4, 2022.

(51) Int. Cl.
*A61B 17/17* (2006.01)
*B33Y 80/00* (2015.01)
*A61B 17/56* (2006.01)
*A61B 17/00* (2006.01)

(52) U.S. Cl.
CPC ............... *A61B 17/17* (2013.01); *B33Y 80/00* (2014.12); *A61B 2017/00526* (2013.01); *A61B 2017/568* (2013.01)

(58) Field of Classification Search
CPC ..... A61B 17/15; A61B 17/17; A61B 17/1735; A61B 2017/568; A61F 2/46; B33Y 80/00
USPC ..................................................... 606/87, 96
See application file for complete search history.

(56) References Cited

U.S. PATENT DOCUMENTS

| 3,872,519 | A | 3/1975 | Giannestras |
| 4,440,835 | A | 4/1984 | Vignaud |
| 4,588,574 | A | 5/1986 | Felder et al. |
| 4,829,152 | A | 5/1989 | Rostoker |

(Continued)

FOREIGN PATENT DOCUMENTS

| CN | 109567913 A | 4/2019 |
| CN | 110090096 | 8/2019 |

(Continued)

OTHER PUBLICATIONS

Larraona et al., "Radiopaque material for 3D printing scaffolds", XXXV Confreso Anual de la Sociedad Espanola de Ingenieria Biomedica. Bilbao, Nov. 29-Dec. 1, 2017, p. 451-454 (Year: 2017).

(Continued)

*Primary Examiner* — Eduardo C Robert
*Assistant Examiner* — Christina Negrelli-Rodriguez
(74) *Attorney, Agent, or Firm* — Husch Blackwell LLP; Bryan D. Stewart; Andrew C. Landsman

(57) ABSTRACT

Provided herein are 3D-printed patient-specific surgical guides and methods for making and using the same. In at least one embodiment, the guides include a first and second end, a first and second side, a conformal bone engaging surface, a front surface, one or more porous regions, one or more walls, and a plurality of openings. At least one of the plurality of openings extends through the guide between the conformal bone engaging surface and the front surface. The conformal bone engaging surface is contoured to a patient's anatomy. The first and second end, and the first and second side are contoured to avoid soft tissues of the patient.

21 Claims, 9 Drawing Sheets

(56) References Cited

U.S. PATENT DOCUMENTS

| | | |
|---|---|---|
| 5,248,456 A | 9/1993 | Evans, Jr. et al. |
| 6,183,519 B1 | 2/2001 | Bonnin |
| 6,419,491 B1 | 7/2002 | Ricci |
| 6,461,358 B1 | 10/2002 | Faccioli |
| 7,001,672 B2 | 2/2006 | Justin et al. |
| 7,468,075 B2 | 12/2008 | Lang et al. |
| 7,534,246 B2 | 5/2009 | Reiley |
| 7,534,263 B2 | 5/2009 | Burdulis, Jr. et al. |
| 7,534,270 B2 | 5/2009 | Ball |
| D595,853 S | 7/2009 | Hanson |
| 7,618,451 B2 | 11/2009 | Berez et al. |
| 7,632,575 B2 | 12/2009 | Justin et al. |
| 7,634,119 B2 | 12/2009 | Tsougarakis et al. |
| 7,666,522 B2 | 2/2010 | Justin et al. |
| 7,717,956 B2 | 5/2010 | Lang |
| D623,749 S | 9/2010 | Horton |
| 7,796,791 B2 | 9/2010 | Tsougarakis et al. |
| 7,799,077 B2 | 9/2010 | Lang et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,077,950 B2 | 12/2011 | Tsougarakis et al. |
| 8,083,745 B2 | 12/2011 | Lang et al. |
| 8,094,900 B2 | 1/2012 | Steines et al. |
| 8,105,330 B2 | 1/2012 | Fitz et al. |
| 8,234,097 B2 | 1/2012 | Steines et al. |
| D653,756 S | 2/2012 | Courtney et al. |
| 8,122,582 B2 | 2/2012 | Burdulis, Jr. et al. |
| 8,142,886 B2 | 3/2012 | Noble et al. |
| 8,337,501 B2 | 12/2012 | Fitz et al. |
| 8,337,507 B2 | 12/2012 | Lang et al. |
| D675,320 S | 1/2013 | Oi |
| 8,343,218 B2 | 1/2013 | Lang et al. |
| 8,366,771 B2 | 2/2013 | Burdulis, Jr. et al. |
| 8,377,129 B2 | 2/2013 | Fitz et al. |
| 8,382,755 B2 | 2/2013 | Austin |
| 8,430,930 B2 | 4/2013 | Hunt |
| 8,439,926 B2 | 5/2013 | Bojarski et al. |
| 8,457,930 B2 | 6/2013 | Schroeder |
| 8,460,304 B2 | 6/2013 | Fitz et al. |
| 8,480,754 B2 | 7/2013 | Bojarski et al. |
| 8,485,820 B1 | 7/2013 | Ali |
| 8,500,740 B2 | 8/2013 | Bojarski et al. |
| 8,529,568 B2 | 9/2013 | Bouadi |
| 8,529,630 B2 | 9/2013 | Bojarski et al. |
| D692,136 S | 10/2013 | Tyber |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,551,173 B2 | 10/2013 | Lechmann et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,617,172 B2 | 12/2013 | Fitz et al. |
| 8,617,242 B2 | 12/2013 | Philipp et al. |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,715,362 B2 | 5/2014 | Reiley |
| 8,735,773 B2 | 5/2014 | Lang |
| D708,747 S | 7/2014 | Curran et al. |
| 8,768,028 B2 | 7/2014 | Lang et al. |
| 8,771,365 B2 | 7/2014 | Bojarski et al. |
| 8,775,133 B2 | 7/2014 | Schroeder |
| 8,828,311 B2 | 9/2014 | Medina et al. |
| 8,843,229 B2 | 9/2014 | Vanasse et al. |
| 8,882,847 B2 | 11/2014 | Burdulis, Jr. et al. |
| 8,888,485 B2 | 11/2014 | Ali |
| 8,906,107 B2 | 12/2014 | Bojarski et al. |
| 8,926,706 B2 | 1/2015 | Bojarski et al. |
| 8,932,363 B2 | 1/2015 | Tsougarakis et al. |
| D722,693 S | 2/2015 | Kaufmann et al. |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,088 B2 | 2/2015 | Tsougarakis et al. |
| 8,974,539 B2 | 3/2015 | Bojarski et al. |
| 8,998,915 B2 | 4/2015 | Fitz et al. |
| 9,020,788 B2 | 4/2015 | Lang et al. |
| 9,023,050 B2 | 5/2015 | Lang et al. |
| 9,034,237 B2 | 5/2015 | Sperry et al. |
| 9,055,953 B2 | 6/2015 | Lang et al. |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| D735,860 S | 8/2015 | Palinchik |
| D736,384 S | 8/2015 | Palinchik |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,125,673 B2 | 9/2015 | Fitz et al. |
| 9,144,500 B2 | 9/2015 | Harding |
| 9,180,015 B2 | 11/2015 | Fitz et al. |
| 9,180,029 B2 | 11/2015 | Hollister et al. |
| 9,186,161 B2 | 11/2015 | Lang et al. |
| 9,186,254 B2 | 11/2015 | Fitz et al. |
| 9,186,257 B2 | 11/2015 | Geisler et al. |
| D745,159 S | 12/2015 | Lin |
| 9,216,025 B2 | 12/2015 | Fitz et al. |
| 9,220,516 B2 | 12/2015 | Lang et al. |
| 9,220,517 B2 | 12/2015 | Lang et al. |
| D747,485 S | 1/2016 | Oi |
| 9,241,724 B2 | 1/2016 | Lang et al. |
| 9,241,725 B2 | 1/2016 | Lang et al. |
| 9,271,845 B2 | 3/2016 | Hunt et al. |
| 9,295,482 B2 | 3/2016 | Fitz et al. |
| 9,295,562 B2 | 3/2016 | Lechmann et al. |
| 9,308,005 B2 | 4/2016 | Fitz et al. |
| 9,308,053 B2 | 4/2016 | Bojarski et al. |
| 9,308,060 B2 | 4/2016 | Ali |
| 9,308,091 B2 | 4/2016 | Lang |
| 9,314,256 B2 | 4/2016 | Fitz et al. |
| 9,320,620 B2 | 4/2016 | Bojarski et al. |
| 9,295,481 B2 | 5/2016 | Fitz et al. |
| 9,326,780 B2 | 5/2016 | Wong et al. |
| 9,333,058 B1 | 5/2016 | Krastev |
| 9,339,279 B2 | 5/2016 | Dubois et al. |
| 9,358,018 B2 | 6/2016 | Fitz et al. |
| 9,364,896 B2 | 6/2016 | Christensen et al. |
| 9,370,426 B2 | 6/2016 | Gabbrielli et al. |
| 9,375,222 B2 | 6/2016 | Fitz et al. |
| 9,387,079 B2 | 6/2016 | Bojarski et al. |
| 9,381,025 B2 | 7/2016 | Fitz et al. |
| 9,402,726 B2 | 8/2016 | Linderman et al. |
| 9,408,615 B2 | 8/2016 | Fitz et al. |
| 9,408,686 B1 | 8/2016 | Miller et al. |
| 9,415,137 B2 | 8/2016 | Meridew |
| 9,421,108 B2 | 8/2016 | Hunt |
| D767,137 S | 9/2016 | Lin |
| 9,433,510 B2 | 9/2016 | Lechmann et al. |
| 9,433,707 B2 | 9/2016 | Swords et al. |
| 9,439,767 B2 | 9/2016 | Bojarski et al. |
| 9,486,226 B2 | 11/2016 | Chao |
| 9,495,483 B2 | 11/2016 | Steines et al. |
| 9,517,134 B2 | 12/2016 | Lang |
| 9,545,317 B2 | 1/2017 | Hunt |
| 9,549,823 B2 | 1/2017 | Hunt et al. |
| 9,561,115 B2 | 2/2017 | Elahinia et al. |

(56) References Cited

U.S. PATENT DOCUMENTS

| | | |
|---|---|---|
| 9,572,669 B2 | 2/2017 | Hunt et al. |
| 9,579,110 B2 | 2/2017 | Bojarski et al. |
| 9,597,197 B2 | 3/2017 | Lechmann et al. |
| 9,603,711 B2 | 3/2017 | Bojarski et al. |
| 9,610,168 B2 | 4/2017 | Terrill |
| 9,636,226 B2 | 5/2017 | Hunt |
| 9,636,229 B2 | 5/2017 | Lang et al. |
| 9,649,178 B2 | 5/2017 | Ali |
| 9,662,157 B2 | 5/2017 | Schneider et al. |
| 9,662,226 B2 | 5/2017 | Wickham |
| 9,668,863 B2 | 6/2017 | Sharp et al. |
| 9,675,465 B2 | 6/2017 | Padovani et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,688,026 B2 | 6/2017 | Ho et al. |
| 9,694,541 B2 | 7/2017 | Pruett et al. |
| 9,700,420 B2 | 7/2017 | Fitz et al. |
| 9,700,971 B2 | 7/2017 | Lang |
| 9,715,563 B1 | 7/2017 | Schroeder |
| 9,737,367 B2 | 8/2017 | Steines et al. |
| 9,750,613 B2 | 9/2017 | Petteys |
| 9,757,235 B2 | 9/2017 | Hunt et al. |
| 9,757,245 B2 | 9/2017 | O'Neil et al. |
| 9,775,680 B2 | 10/2017 | Bojarski et al. |
| 9,782,270 B2 | 10/2017 | Wickham |
| 9,788,972 B2 | 10/2017 | Flickinger et al. |
| 9,849,019 B2 | 12/2017 | Miller et al. |
| 9,872,773 B2 | 1/2018 | Lang et al. |
| 9,877,790 B2 | 1/2018 | Bojarski et al. |
| D809,661 S | 2/2018 | Mueller et al. |
| 9,907,670 B2 | 3/2018 | Deridder et al. |
| 9,910,935 B2 | 3/2018 | Golway et al. |
| 9,913,723 B2 | 3/2018 | Fitz et al. |
| 9,918,849 B2 | 3/2018 | Morris et al. |
| 9,925,054 B2 | 3/2018 | Siegler |
| 9,943,370 B2 | 4/2018 | Asseln et al. |
| 9,943,627 B2 | 4/2018 | Zhou et al. |
| 9,949,839 B2 | 4/2018 | Sander |
| 9,956,047 B2 | 5/2018 | Bojarski et al. |
| 9,956,048 B2 | 5/2018 | Bojarski et al. |
| D829,909 S | 10/2018 | Horton |
| 10,085,839 B2 | 10/2018 | Wong et al. |
| D835,278 S | 12/2018 | Gottlieb |
| 10,183,442 B1 | 1/2019 | Miller |
| 10,245,152 B2 | 4/2019 | Kloss |
| D849,944 S | 5/2019 | Dacosta |
| 10,278,823 B1 | 5/2019 | Xue |
| D850,620 S | 6/2019 | Tyber |
| D855,184 S | 7/2019 | Predick |
| 10,357,377 B2 | 7/2019 | Nyahay |
| D858,769 S | 9/2019 | Barela et al. |
| 10,449,051 B2 | 10/2019 | Hamzey |
| 10,492,686 B2 | 12/2019 | Hunter |
| D877,907 S | 3/2020 | Linder et al. |
| D878,589 S | 3/2020 | Linder |
| D878,590 S | 3/2020 | Linder et al. |
| D879,295 S | 3/2020 | Abbasi |
| D879,961 S | 3/2020 | Linder et al. |
| D881,665 S | 4/2020 | Zemel et al. |
| 10,624,746 B2 | 4/2020 | Jones et al. |
| 10,667,924 B2 | 6/2020 | Nyahay |
| 10,744,001 B2 | 8/2020 | Sack |
| 10,772,732 B1 | 9/2020 | Miller et al. |
| D899,900 S | 10/2020 | Blanco |
| 10,940,015 B2 | 3/2021 | Sack |
| D920,515 S | 5/2021 | Miller |
| D920,516 S | 5/2021 | Miller |
| D920,517 S | 5/2021 | Miller |
| 11,026,798 B1 | 6/2021 | Miller |
| 11,033,394 B2 | 6/2021 | Hamzey |
| 11,135,771 B1 | 10/2021 | Reith |
| D938,033 S | 12/2021 | Dang |
| 11,324,525 B1 | 5/2022 | Garvey |
| 11,353,277 B2 | 6/2022 | Muceus |
| 11,439,726 B2 | 9/2022 | Spence |
| 11,471,203 B2 | 10/2022 | Sutika |
| 2004/0148032 A1 | 7/2004 | Rutter et al. |
| 2006/0249875 A1 | 11/2006 | Robb et al. |
| 2007/0100346 A1 | 5/2007 | Wyss |
| 2007/0118243 A1 | 5/2007 | Schroeder et al. |
| 2008/0206297 A1 | 8/2008 | Roeder et al. |
| 2009/0093668 A1 | 4/2009 | Marten et al. |
| 2009/0182430 A1 | 7/2009 | Tyber et al. |
| 2010/0137990 A1 | 6/2010 | Apatsidis et al. |
| 2010/0168798 A1 | 7/2010 | Clineff et al. |
| 2010/0286791 A1 | 11/2010 | Goldsmith |
| 2011/0144752 A1 | 6/2011 | Defelice et al. |
| 2011/0190898 A1 | 8/2011 | Lenz |
| 2011/0224796 A1 | 9/2011 | Weiland et al. |
| 2011/0230974 A1 | 9/2011 | Musani |
| 2012/0064288 A1 | 3/2012 | Nakano et al. |
| 2012/0215310 A1 | 8/2012 | Sharp et al. |
| 2013/0068968 A1 | 3/2013 | Daniel |
| 2013/0123935 A1 | 5/2013 | Hunt et al. |
| 2013/0158651 A1 | 6/2013 | Hollister et al. |
| 2013/0197657 A1 | 8/2013 | Anca et al. |
| 2013/0218282 A1 | 8/2013 | Hunt |
| 2013/0274890 A1 | 10/2013 | Mckay |
| 2013/0296874 A1 | 11/2013 | Chao |
| 2014/0100779 A1 | 4/2014 | Tuke |
| 2014/0107785 A1 | 4/2014 | Geisler et al. |
| 2014/0107786 A1 | 4/2014 | Geisler et al. |
| 2014/0236299 A1 | 8/2014 | Roeder et al. |
| 2014/0277443 A1 | 9/2014 | Fleury et al. |
| 2014/0277452 A1 | 9/2014 | Skaer |
| 2014/0288650 A1 | 9/2014 | Hunt |
| 2014/0336680 A1 | 11/2014 | Medina et al. |
| 2014/0350688 A1 | 11/2014 | Michel |
| 2014/0371863 A1 | 12/2014 | Vanasse et al. |
| 2015/0105858 A1 | 4/2015 | Papay et al. |
| 2015/0282945 A1 | 10/2015 | Hunt |
| 2015/0282946 A1 | 10/2015 | Hunt |
| 2015/0320461 A1 | 11/2015 | Ehmke |
| 2015/0335434 A1 | 11/2015 | Patterson et al. |
| 2015/0343709 A1 | 12/2015 | Gerstle et al. |
| 2015/0351915 A1 | 12/2015 | Defelice et al. |
| 2016/0008139 A1 | 1/2016 | Siegler |
| 2016/0051371 A1 | 2/2016 | Defelice et al. |
| 2016/0089138 A1 | 3/2016 | Early et al. |
| 2016/0151833 A1 | 6/2016 | Tsao |
| 2016/0193055 A1 | 7/2016 | Ries |
| 2016/0199193 A1 | 7/2016 | Willis et al. |
| 2016/0213485 A1 | 7/2016 | Schaufler et al. |
| 2016/0213486 A1 | 7/2016 | Nunley et al. |
| 2016/0213487 A1* | 7/2016 | Wilson .............. A61F 2/4465 |
| 2016/0213488 A1 | 7/2016 | Moore et al. |
| 2016/0220288 A1 | 8/2016 | Dubois et al. |
| 2016/0256279 A1 | 9/2016 | Sanders et al. |
| 2016/0256610 A1 | 9/2016 | Zhou et al. |
| 2016/0270931 A1 | 9/2016 | Trieu |
| 2016/0287388 A1 | 10/2016 | Hunt et al. |
| 2016/0303793 A1 | 10/2016 | Ermoshkin et al. |
| 2016/0333152 A1 | 11/2016 | Cook et al. |
| 2016/0374829 A1* | 12/2016 | Vogt ................. A61F 2/4455 623/17.16 |
| 2017/0014169 A1 | 1/2017 | Dean et al. |
| 2017/0020685 A1 | 1/2017 | Geisler et al. |
| 2017/0036403 A1 | 2/2017 | Ruff et al. |
| 2017/0042697 A1 | 2/2017 | Mcshane, III et al. |
| 2017/0056178 A1 | 3/2017 | Sharp et al. |
| 2017/0056179 A1 | 3/2017 | Lorio |
| 2017/0066873 A1 | 3/2017 | Gardet |
| 2017/0105844 A1 | 4/2017 | Kuyler et al. |
| 2017/0156880 A1 | 6/2017 | Halverson et al. |
| 2017/0165085 A1 | 6/2017 | Lechmann et al. |
| 2017/0165790 A1 | 6/2017 | Mccarthy et al. |
| 2017/0172758 A1 | 6/2017 | Field et al. |
| 2017/0182222 A1 | 6/2017 | Paddock et al. |
| 2017/0018919 A1 | 7/2017 | Reiley |
| 2017/0209274 A1 | 7/2017 | Beerens et al. |
| 2017/0216035 A1 | 8/2017 | Hunt |
| 2017/0216036 A1 | 8/2017 | Cordaro |
| 2017/0239054 A1 | 8/2017 | Engstrand et al. |

(56) References Cited

U.S. PATENT DOCUMENTS

| | | |
|---|---|---|
| 2017/0239064 A1 | 8/2017 | Cordaro |
| 2017/0245998 A1 | 8/2017 | Padovani et al. |
| 2017/0252165 A1 | 9/2017 | Sharp et al. |
| 2017/0258606 A1 | 9/2017 | Afzal |
| 2017/0282455 A1 | 10/2017 | Defelice et al. |
| 2017/0296244 A1 | 10/2017 | Schneider et al. |
| 2017/0319344 A1 | 11/2017 | Hunt |
| 2017/0323037 A1 | 11/2017 | Schroeder |
| 2017/0333205 A1 | 11/2017 | Joly et al. |
| 2017/0354510 A1 | 12/2017 | O'Neil et al. |
| 2017/0354513 A1 | 12/2017 | Maglaras et al. |
| 2017/0355815 A1 | 12/2017 | Becker et al. |
| 2017/0360488 A1 | 12/2017 | Kowalczyk et al. |
| 2017/0360563 A1 | 12/2017 | Hunt et al. |
| 2017/0360578 A1 | 12/2017 | Shin et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0008419 A1 | 1/2018 | Tyber et al. |
| 2018/0022017 A1 | 1/2018 | Fukumoto et al. |
| 2018/0064540 A1 | 3/2018 | Hunt |
| 2018/0085230 A1 | 3/2018 | Hunt |
| 2018/0098858 A1 | 4/2018 | Valderraband |
| 2018/0104063 A1* | 4/2018 | Asaad .................. A61F 2/447 |
| 2018/0110593 A1 | 4/2018 | Khalil |
| 2018/0110626 A1 | 4/2018 | Mcshane, III et al. |
| 2018/0110627 A1 | 4/2018 | Sack |
| 2018/0117219 A1 | 5/2018 | Yang et al. |
| 2018/0147319 A1 | 5/2018 | Colucci-Mizenko et al. |
| 2018/0280140 A1 | 10/2018 | Jones |
| 2018/0289380 A1 | 10/2018 | Mauldin |
| 2018/0289515 A1 | 10/2018 | Nemes et al. |
| 2019/0167433 A1 | 6/2019 | Allen |
| 2019/0262101 A1 | 8/2019 | Shanjani et al. |
| 2019/0343652 A1 | 11/2019 | Petersheim et al. |
| 2020/0000595 A1 | 1/2020 | Jones |
| 2020/0030102 A1 | 1/2020 | Mullens et al. |
| 2020/0046512 A1 | 2/2020 | Newman et al. |
| 2020/0085452 A1 | 3/2020 | Siegler |
| 2020/0085585 A1 | 3/2020 | Siegler |
| 2020/0155321 A1 | 5/2020 | Dikovsky |
| 2020/0171752 A1 | 6/2020 | Rogren |
| 2020/0171753 A1 | 6/2020 | Satko |
| 2020/0367910 A1 | 11/2020 | Hafez et al. |
| 2021/0077276 A1 | 3/2021 | Garvey et al. |
| 2021/0216683 A1 | 7/2021 | Rai |
| 2021/0298908 A1 | 9/2021 | Holmes |
| 2021/0340334 A1 | 11/2021 | Portela |
| 2022/0023048 A1 | 1/2022 | Nolens |
| 2022/0087670 A1 | 3/2022 | Selmoune |
| 2022/0134639 A1 | 5/2022 | Allen |
| 2022/0142783 A1 | 5/2022 | Ahmadi |
| 2022/0168109 A1 | 6/2022 | Giordano |
| 2022/0296386 A1 | 9/2022 | Fang |

FOREIGN PATENT DOCUMENTS

| | | |
|---|---|---|
| DE | 69806985 | 6/2003 |
| EP | 1180989 | 4/2006 |
| EP | 2832321 | 2/2015 |
| EP | 2635239 | 7/2017 |
| EP | 2913030 | 3/2018 |
| EP | 3586800 | 1/2020 |
| FR | 3071400 | 3/2019 |
| JP | 4840886 | 12/2011 |
| KR | 301007894 | 5/2019 |
| WO | 2014020562 | 2/2014 |
| WO | 2020123295 A1 | 6/2020 |

OTHER PUBLICATIONS

Rozema et al., The effects of different steam-sterilization programs on material properties of poly(l-lactide), Journal of Applied Biomaterials, vol. 2, 23-28 (1991) (Year: 1991).

Alt, Sami. "Design for Sterilization Part 1: Steam Sterillization." Material, Material Technology Blog, Jun. 3, 2016, www.material-technology.com/single-post/2016/05/24/Design-for-Sterilization-part-1-Steam-Sterillization.

Ducheyne, Paul. "Comprehensive Biomaterials." Comprehensive Biomaterials, vol. 1, Elsevier, 2011, pp. 135-135.

Anat Ratnovsky et al., Mechanical Properties of Different Airway Stents, Med. Eng'g. Physics, Mar. 2011, at 408., http://www.medengphys.com/article/S1350-4533(15)00042-9/fulltext.

Andrew T. Miller et al., Fatigue of Injection Molded and 3D Printed Polycarbonate Urethane in Solution, 108 Polymer 121 (2017).

Andrew T. Miller et al., Deformation and Fatigue of Tough 3D Printed Elastomer Scaffolds Processed by Fused 3 Deposition Modeling and Continuous Liquid Interface Production, 75 J. Mechanical Behavior Biomedical Materials 1 (2017).

Ortho Spine News, "SeaSpine Announces 25,000th NanoMetalene Implantation", first available Dec. 18, 2019. (https://orthospinenews.com/2019/12/18/seaspine-announces-25000th-nanometalene-implantation/) (Year: 2019).

Restor3d, "Products", first available Sep. 28, 2020. (https://web.archive.org/web/20200928123335/https:/restor3d.com/products) (Year: 2020).

Ortho Spine News, "Nvision Biomedical Technologies: First FDA Clearance for Osteotomy Wedge System", first available Oct. 28, 2020. (https://orthospinenews.com/2020/10/28/nvision-biomedical-technologies-first-fda-clearance-for-osteotomy-wedge-system-made-of-peek-optima-ha-enhanced/) (Year: 2020).

Sina, "Application logic of triple periodic minimum surface", first available Oct. 24, 2020. (https://k.sina.com.cn/article_2422410454_90630cd6001 00tlbm.html?from=science) (Year: 2020).

3D Adept Media, "Johnson & Johnson Medical", first available Sep. 17, 2018. (https://3dadept.com/johnson-johnson-medical-has-acquired-3d-printed-spmplants-special ist-emerging-implant-technologies/) (Year: 2018).

Additive Orthopaedics, "Additive Orthopaedics 3d Printed Cotton Bone Segment", first available Sep. 19, 2020. (https://web.archive.org/web/20200919145251/https:/www.additiveorthopaedics.com/our-products/cotton/) (Year: 2020).

Indiamart, "Anterior Cervical Fusion Cage for Spine Surgery", first accessed Dec. 9, 2020. (https://www.indiamart.com/proddetail/anterior-cervical-fusion-cage-12402896897 .html) (Year: 2020).

Instagram, "restor3d", first available Jul. 21, 2020. (https://www.instagram.com/p/CC6dztOAKcM/?utm_source=ig_web_link) (Year: 2020).

Extended European Search Report dated Feb. 12, 2021 for European Patent Application No. EP20196410.3.

* cited by examiner

SURGICAL GUIDES AND PROCESSES FOR PRODUCING AND USING THE SAME

CROSS REFERENCE TO RELATED APPLICATIONS

This application claims the benefit of and priority to U.S. Provisional Patent Application No. 63/413,189 filed Oct. 4, 2022, entitled "SURGICAL GUIDES AND PROCESSES FOR PRODUCING AND USING THE SAME," which is incorporated herein by reference in its entirety.

BACKGROUND

Surgical guides may be used to align patient anatomy for bone resection in various orthopedic surgeries such as total or partial joint replacements (e.g., ankle, knee, shoulder, hip, toe, or elbow joint replacements, among others.). Accurate bone resection relates to implant performance because implants are placed to appose the remaining bone. As such, ensuring that a surgical guide remains in a desired position may be important because incorrect positioning between the guide and bone may cause inaccurate bone resection and therefore inaccurate implant placement, which, in turn, may cause poor implant performance and premature failure. Current surgical guides may be relatively smooth-surfaced and constructed from smooth materials such as plastic, thus exhibiting negative surface roughness and increasing the likelihood of slippage.

As a result, there is a long-felt, but unsolved need for improved surgical guides for orthopedic surgeries and methods of producing and installing the same.

BRIEF SUMMARY OF THE DISCLOSURE

Briefly described, aspects of the present disclosure generally relate to patient-specific surgical guides configured to assist in the positioning of other intraoperative devices and prevent the guide itself from slipping when in contact with a patient bone, as well as processes for making and using the same. According to a first aspect, the present disclosure relates to a patient-specific surgical guide comprising a 3D-printed body comprising (i) a metallic material; (ii) a front surface; (iii) a conformal bone engaging surface opposite the front surface and contoured to a patient's anatomy, the conformal bone engaging surface comprising one or more gyroid structure regions; and (iv) a plurality of openings extending through the 3D-printed body between the conformal bone engaging surface and the front surface, wherein: at least one of the plurality of openings is sized to receive a surgical instrument for resecting a portion of the patient's anatomy; and the one or more gyroid structure regions comprise: i) an average pore depth of 0.2 mm to 2.0 mm; and ii) a minimum feature size of 0.1 mm to 2 mm.

According to a second aspect, the patient-specific surgical guide of the first aspect or any other aspect, wherein at least one of the gyroid structure regions has an effective radius of 0.5 mm to 1 mm.

According to a third aspect, the patient-specific surgical guide of the second aspect or any other aspect, wherein: the 3D-printed body comprises one or more walls; and at least one of the plurality of openings extends through the one or more walls.

According to a fourth aspect, the patient-specific surgical guide of the third aspect or any other aspect, wherein: the 3D-printed body comprises a first end, a second end, a first side, and a second side; and the first end, the second end, the first side, and the second side are contoured to avoid at least one soft tissue structure of the patient's anatomy.

According to a fifth aspect, the patient-specific surgical guide of the fourth aspect or any other aspect, wherein the at least one of the plurality of openings is an elongate slot.

According to a sixth aspect, the patient-specific surgical guide of the fifth aspect or any other aspect, wherein the surgical instrument comprises a saw blade.

According to a seventh aspect, the patient-specific surgical guide of the sixth aspect or any other aspect, wherein one or more of the plurality of openings is a structural opening.

According to an eighth aspect, the patient-specific surgical guide of the sixth aspect or any other aspect, wherein one or more of the plurality of openings is a securement hole.

According to a ninth aspect, the patient-specific surgical guide of the sixth aspect or any other aspect, wherein one or more of the plurality of openings is an alignment hole.

The present disclosure also relates to a surgical guide that, in some embodiments, advantageously adheres to bone surfaces, such as, for example, a partially to fully rough-surfaced talar resection guide. According to a tenth aspect, the present disclosure related to a patient-specific surgical guide comprising (i) a rigid material; (ii) a front surface; (iii) a conformal bone engaging surface opposite the front surface and contoured to a patient's anatomy, the conformal bone engaging surface comprising one or more porous regions; and (iv) a plurality of openings extending through the 3D-printed body between the conformal bone engaging surface and the front surface, wherein: at least one of the plurality of openings is sized to receive a surgical instrument for resecting a portion of the patient's anatomy; and the one or more porous regions comprise an average pore depth of 0.2 mm to 2.0 mm.

According to an eleventh aspect, the patient-specific surgical guide of the tenth aspect or any other aspect, wherein: the 3D-printed body comprises a first end, a second end, a first side, and a second side; and the first end, the second end, the first side, and the second side are contoured to avoid at least one soft tissue structure of the patient's anatomy.

According to a twelfth aspect, the patient-specific surgical guide of the eleventh aspect or any other aspect, wherein at least one of the one or more porous regions has an effective radius of 0.5 mm to 1 mm.

According to a thirteenth aspect, the patient-specific surgical guide of the twelfth aspect or any other aspect, wherein at least one of the one or more porous regions has a minimum feature size of 0.1 mm to 2 mm.

According to a fourteenth aspect, the patient-specific surgical guide of the thirteenth aspect or any other aspect, wherein the one or more porous regions comprise a gyroid structure.

According to a fifteenth aspect, the patient-specific surgical guide of the fourteenth aspect or any other aspect, wherein the rigid material comprises a metallic material.

According to a sixteenth aspect, the patient-specific surgical guide of the fifteenth aspect or any other aspect, wherein the at least one opening of the plurality of openings is an elongate slot.

According to a seventeenth aspect, the patient-specific surgical guide of the sixteenth aspect or any other aspect, wherein one or more of the plurality of openings is a structural opening.

According to an eighteenth aspect, the patient-specific surgical guide of the sixteenth aspect or any other aspect, wherein one or more of the plurality of openings is a securement hole.

According to a nineteenth aspect, the patient-specific surgical guide of the sixteenth aspect or any other aspect, wherein one or more of the plurality of openings is an alignment hole.

The present disclosure also relates to a method for using a patient-specific surgical guide and comprising, according to a twentieth aspect, (i) receiving a 3D-printed patient-specific surgical guide, the patient-specific surgical guide comprising (a) a rigid material; (b) a front surface; (c) a conformal bone engaging surface opposite the front surface and contoured to patient anatomy, the conformal bone engaging surface comprising one or more porous regions; the one or more porous regions comprising an average pore depth of 0.2 mm to 2.0 mm; and a minimum feature size of 0.1 mm to 2 mm; (d) a plurality of openings extending through the 3D-printed body between the conformal bone engaging surface and the front surface and sized to receive a surgical instrument for resecting a portion of the patient anatomy; (ii) intraoperatively engaging the conformal bone engaging surface with the patient anatomy; (iii) inserting the surgical instrument through the elongate slot; and (iv) resecting a portion of the patient anatomy based on the placement of the patient-specific surgical guide.

According to a twenty-first aspect, the method of the twentieth aspect or any other aspect, further comprising the step of pressing at least one of the one or more porous regions of the patient-specific surgical guide onto soft tissues surrounding the patient anatomy.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

DETAILED DESCRIPTION

Figure 1:
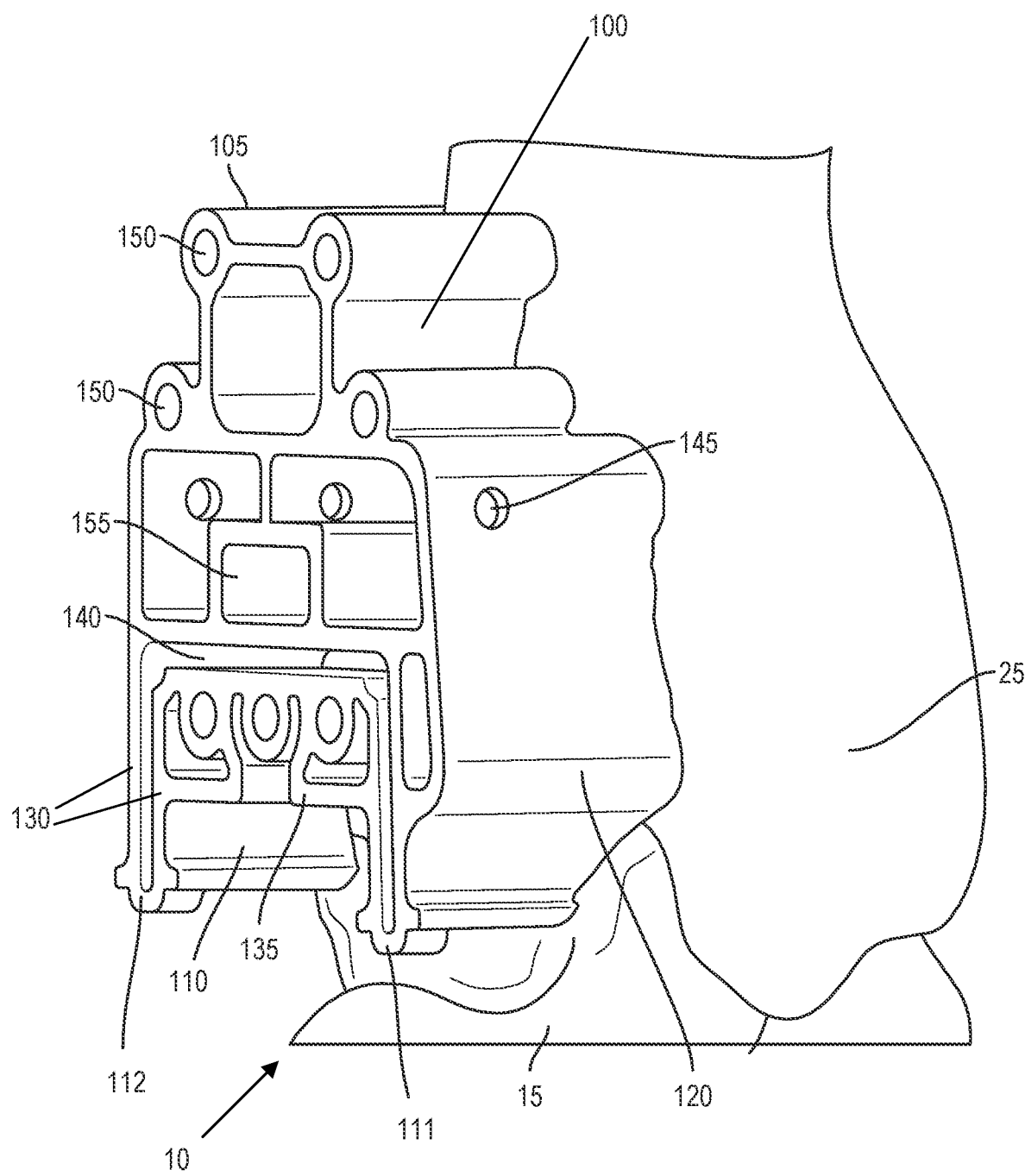
FIG. 1 is a perspective view of an exemplary tibial resection guide, according to one embodiment.

According to particular embodiments, this disclosure relates to surgical guides with features for improved contact between the guide and a patient bone or bones. It may be advantageous to increase the frictional fit between the guide and patient bones to help prevent guide creep or motion that may affect cut accuracy. For example, if a guide is precisely aligned with patient anatomy to remove a portion of patient bone and then the guide moves slightly, the user may make an imprecise cut with the slightly misaligned guide and a corresponding patient-specific implant may not fit as well.

Further, patient-specific guides may be produced to provide accurate bone removal for installation of patient-specific implants. Patient-specific surgical guides are designed to contact the patient's bone and to sit in a specific position to define the position of the bone resection relative to the patient's anatomy. For example, when performing an ankle arthroplasty or arthrodesis, the optimal location for placing the surgical guide may be on a relatively smooth surface of the underlying bone, and it may be challenging to maintain accurate placement of the surgical guide throughout the bone resection procedure due to a relatively low coefficient of friction between the guide and the smooth bone surface.

The surgical guide may be constructed from any suitable material. In at least one embodiment, the surgical guide is 3D-printed or otherwise created via additive manufacturing in a metallic material, including, but not limited to titanium, stainless steel, or cobalt chrome. In certain embodiments, the material selection may be beneficial under medical imaging techniques (e.g., CT scanning, X-rays) and may cause the guide to be visible in contrast to underlying patient anatomy. According to particular embodiments, the surgical guide includes a plurality of materials, each material associated with a different region or level of roughness or porosity. In embodiments where the guide is constructed from one or more materials, certain areas or macroscopic features of the guide may appear differently under medical imaging/fluoroscopic techniques, thereby alerting the user to the positioning of various fixation features.

Pre-operative planning of resection surgeries may be assisted by patient imaging (e.g., CT scans, MRIs, X-rays, etc.), thus allowing a user to define the desired implant placement and corresponding bone resection for the particular patient anatomy. In these embodiments (and others), a user and/or a device guide manufacturer may perform the following steps: access the patient imaging scan, evaluate its parameters for acceptability, segment the scan, create 3D reconstructions of the scanned anatomy (such as in a CAD environment), and then employ 3D printing techniques, among other manufacturing techniques, to create the surgical guide.

The resulting guide contains patient-matched surfaces which are used by the user to aid in the placement of preoperative and intraoperative instruments, thereby ensuring accurate placement of intraoperative instruments and of the surgical guide itself. The user may then adjust the position of the instruments according to various degrees of freedom to achieve a final position, and may then proceed with the rest of the orthopedic procedure. In some embodiments, the surgical guide may comprise various walls and openings according to patient-specific needs and resulting in an at least partial polygonal, angular, convex, concave, or otherwise suitable shape. In other embodiments, the surgical guide may be entirely patient-specific such that the guide encompasses an organic shape of varying thicknesses (e.g., without walls and/or hard angles and comprising minimal material).

In various embodiments, the surgical guide discussed herein includes a porous or otherwise textured structure (e.g., a triply periodic minimal surface (TPMS) structure, including, but not limited to, a gyroid structure; or a pattern of geometric shapes embossed onto a surface) to increase the anisotropic frictional force (e.g., frictional fit, expulsion resistance, sheer force, gripping force, etc.) between bone and the guide. In some embodiments, the surgical guide includes other features for guiding surgical instruments (e.g., saw blades, bone mills, drills, burrs, reamers, etc.) for resecting the bone where the guide is fixed in place to prevent its motion relative to the bone and other certain surgical instruments cutting or resecting the bone. In various embodiments, the surgical guide includes features that enable a user to view different portions of patient anatomy, or mark or otherwise note different patient anatomical features which may help the user place an implant.

In at least one embodiment, the surgical guide includes a smooth region and a porous region that may additionally include a gyroid structure region. The surgical guide mates with underlying patient anatomy wherein a patient-contacting surface, or conformal bone engaging surface, of the guide at least partially includes a porous structure. In various embodiments, the depth of porosity is a function of the potential thickness of soft tissue on an exterior of bone plus an additional depth factor. In some embodiments, the porous portions of the conformal bone engaging surface may have an average depth between 0.2 mm and 2 mm. The porous regions may be defined as a function of minimum feature size (e.g., wall thickness, geometric features, etc.) in a range of 0.1 mm to 2 mm. In one or more embodiments, the porous region may have an "aspect ratio" defined by the depth of the porous region relative to the effective radius of the porous region, the latter of which may be between 0.5 mm and 1 mm. Depending on the use case (e.g., upper extremities, lower extremities, etc.) or on the type of patient anatomy to be contacted by the guide (e.g., bones, osteophytes, etc.), the aspect ratio may be increased or decreased. In some embodiments, cartilage, periosteum, and other soft tissues are not contacted by the guide.

According to one or more embodiments, the patient-facing surface may include an entirely porous and/or gyroid structure. In other embodiments, some but not all portions of the patient-facing surface may include a porous and/or gyroid structure. The porous and/or gyroid structures of patient-facing surfaces of alternative embodiments may be between 15 and 85 percent of the patient-facing surface area. Thus, during an orthopedic procedure, the depth of the porous region and the overall aspect ratio may improve the positional stability of the surgical guide due to increased resistance to lateral displacement forces and increased anisotropic frictional force between the guide and the patient anatomy, the latter of which may include a variety of tissue structures.

The surgical guide may include certain macroscopic features that may help the user in performing orthopedic surgeries. For example, the surgical guide may include through-hole openings along any portion of its surface for nails, screws, K-wires, or any other suitable object to secure the guide in an optimal position on an underlying patient bone. Some embodiments may include through-slots that may be used to guide surgical instruments (e.g., oscillating saws, drills, drill burs, etc.) on prescribed paths along the underlying bone. Additionally, there may be alignment holes along any surface of the surgical guide that may assist in additional positional adjustments of surgical guide placement. In at least one embodiment, the overall guide size is correlated with patient-specific anatomy.

The above features (and others) will be discussed herein in the context of specific surgical guide types (e.g., an ankle resection guide). However, it will be understood that the concepts discussed here are applicable to any suitable surgical guide used anywhere in a human (or other animal), such as the hands, feet, shoulders, knees, elbows, face, head, arms, legs, hips, pelvis, spine, back, etc., and are applicable to any procedure or surgical guide, including those for bunion surgery (e.g., Lapidus fusion) and like procedures.

Figure 2:
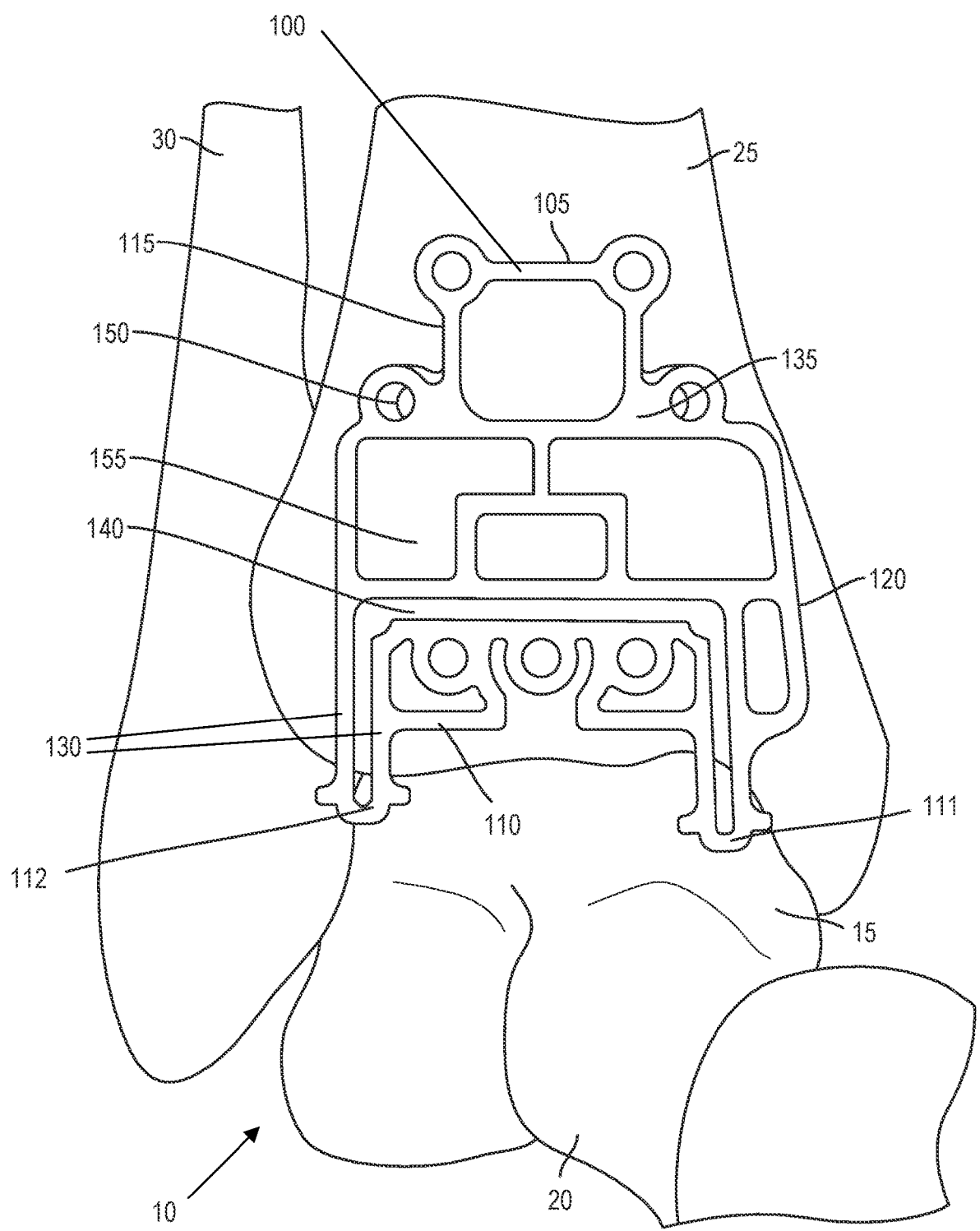
FIG. 2 is a side view of the exemplary tibial resection guide of FIG. 1, according to one embodiment.

Referring now to the drawing figures, FIGS. 1 and 2 show an exemplary surgical guide 100. In this embodiment, the surgical guide 100 is a tibial resection guide and is aligned with a patient ankle joint 10. A human ankle joint 10 is the area where the foot and the leg meet, and includes three bones that join together to form a hinge joint. Tibia 25 and fibula 30 connect from the knee to the ankle, acting as a mortise and forming the top of the hinge joint in which the body of a talus 15 fits (the lower part of the ankle), and which acts as a tenon. The ankle includes three smaller joints: the talocrural joint, the subtalar joint, and the inferior tibiofibular joint. The movements produced at the ankle joint 10 are dorsiflexion and plantarflexion of the foot.

In the embodiment shown, the surgical guide 100 includes a first end 105 and a second end 110, where the first end 105 is placed over a portion of the tibia 25 and next to the fibula 30, and the second end 110 is placed over a portion of the tibia 25 and next to the talus 15 such that the second end 110 avoids contact with patient cartilage. The surgical guide 100 also includes a first side 115 and a second side 120, where the first side 115 is positioned toward a lateral side of the ankle joint 10 and the second side 120 is positioned toward a medial side of the ankle joint 10. As will be discussed with reference to FIG. 3, a conformal bone engaging surface 125, which may be patient-specific, contacts one or more of the aforementioned bones of the ankle joint 10.

In various embodiments, the second end 110 may be pronged or otherwise constructed in order to avoid contact with soft tissues such as cartilage. The second end 110 includes two prongs 111, 112 spaced substantially near the medial and lateral sides of the talus 15. The prongs 111, 112 may aid in the positioning of the guide 100 over the tibia 25 such that the guide 100 is flush against the tibia 25, and avoids contact with soft tissues and the talus 15. In alternate embodiments, there may be any suitable number of prongs or other support structures at any suitable spacing intervals on the second end 110 in accordance with the principles of this disclosure.

In the embodiments shown in FIGS. 1 and 2, the surgical guide 100 defines one or more structural openings 155. The one or more structural openings 155 are located on a front surface 135 of the surgical guide 100, and extend through the body of the guide 100 and to a conformal bone engaging surface (shown in FIG. 3), forming one or more walls 130. The one or more structural openings 155 shown in FIGS. 1 and 2 are generally of a polygonal shape, but in other embodiments they may be any suitable shape or size to form walls of any suitable shape, size, and/or thickness. Additionally, the one or more structural openings 155 may aid in the structural integrity of the guide 100, reduce compositional material usage, or serve any other suitable purpose.

The surgical guide 100 may include a front surface 135 that may be generally planar or have a contour that conforms to the patient (e.g., in a guide that is used in a procedure where both sides of a guide contact patient anatomy. The front surface 135 may include one or more slots 140. The one or more slots 140 may have a length longer than their width, and extend through the body of the guide 100 to a bone engaging surface. The one or more slots 140 may be situated on any portion of the front surface 135 without departing from the principles of this disclosure, generally wherever a user may find it beneficial to access and/or resect portions of the patient's bone visible through the one or more slots 140. In at least one embodiment, the one or more slots 140 may be beneficial for various resection techniques, allowing a user to use a variety of surgical equipment. As will be discussed with reference to FIG. 3, the one or more slots 140 may be at least partially defined by various dimensions including depth and length.

The front surface 135 may include one or more securement holes 150. The one or more securement holes 150 may have a circular or ovular shape, and extend through the guide 100 to a conformal bone engaging surface (shown in FIG. 3). The one or more securement holes 150 may be positioned on any portion of the front surface 135 without departing from the principles of this disclosure, generally wherever a user may find it beneficial to secure the guide 100 to the patient bone. In at least one embodiment, the one or more securement holes 150 may be beneficial for securing the surgical guide 100 in place through use of equipment including, but not limited to, K-wires, nails, screws, or any other suitable attachment mechanism. As will be discussed with reference to FIG. 3, the one or more securement holes 150 may be at least partially defined by various dimensions including depth and length.

The surgical guide 100 may further include one or more alignment holes 145. The one or more alignment holes 145 have a generally circular or ovular shape and extend through various walls of the surgical guide (further discussed with FIG. 4). The one or more alignment holes 145 may generally be aligned with respect to each other, thereby allowing a user to utilize the one or more alignment holes 145 to accurately position the surgical guide 100 and/or other surgical equipment, amongst serving other purposes. As will be discussed with reference to FIG. 4, the one or more alignment holes 145 may be at least partially defined by various dimensions including depth and length.

Figure 3:
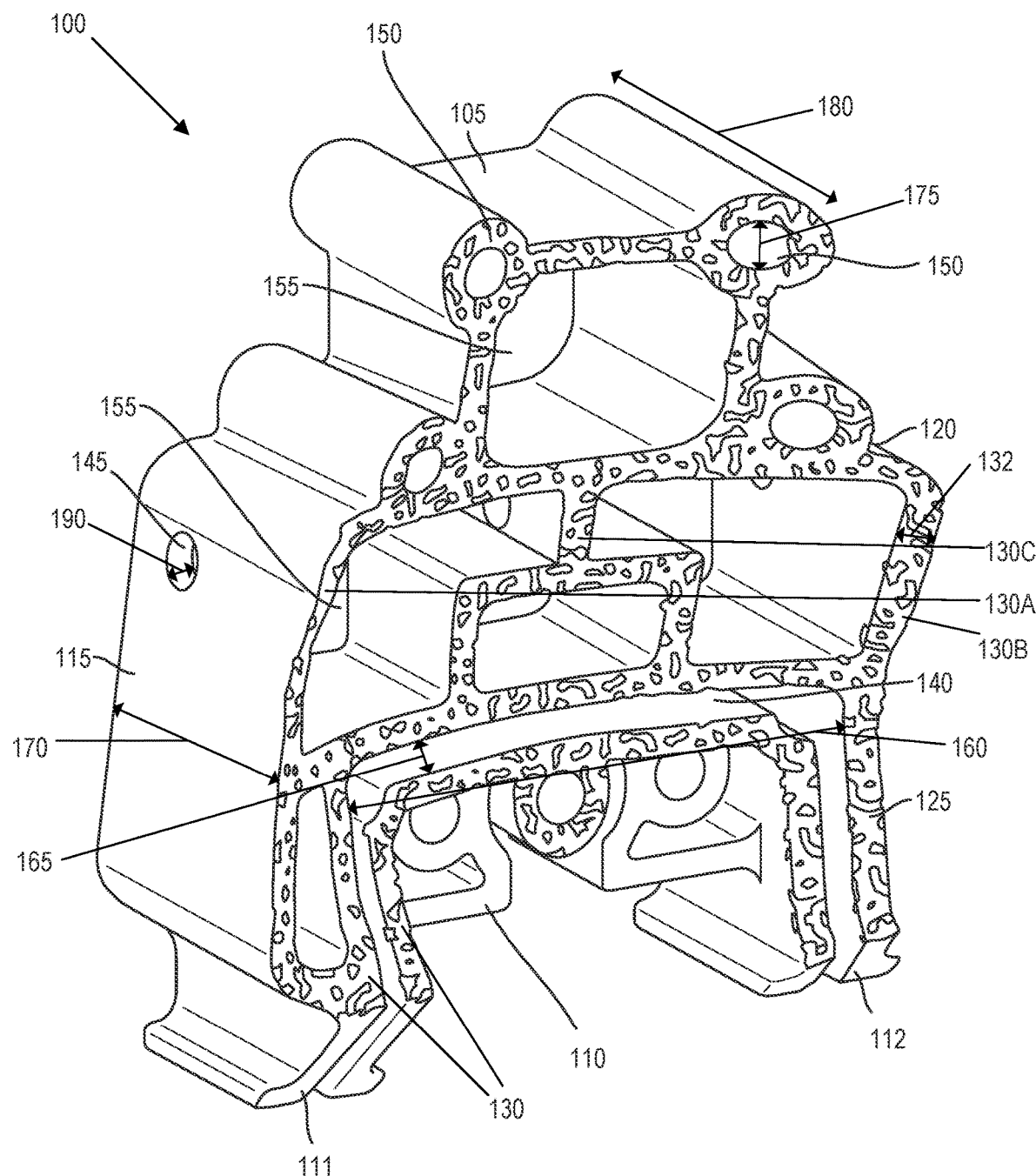
FIG. 3 is a perspective view of the exemplary tibial resection guide of FIG. 1, showing the guide mounted to a bone surface, according to one embodiment.

Turning now to FIG. 3, the conformal bone engaging surface 125 of the surgical guide 100 is shown. In some embodiments, the conformal bone engaging surface 125 exhibits a relatively rough texture in relation to other surfaces of the surgical guide 100. In one or more embodiments, the conformal bone engaging surface 125 is a porous surface and may optionally include a gyroid structure or any other suitable design without departing from the principles of this disclosure. The porous surface may be beneficial for keeping the surgical guide 100 in place during an orthopedic procedure (in case of guide 100 slippage) due to its texture, thus the surface 125 may exhibit a relatively high anisotropic resistance to various forces. The porous surface structure (and/or the entire guide 100) may be 3D printed to obtain a high degree of customizability in the surgical guide 100 for different patient applications.

In various embodiments, the surgical guide 100 includes one or more walls 130 (including, but not limited to, 130A, 130B, 130C), each of which may have a wall thickness 132 measuring between about 1.0-2.0 mm, or about 2.0-3.0 mm, or about 3.0-4.0 mm, or about 4.0-5.0 mm. Generally speaking, walls forming the area around the one or more securement holes 150 may vary in thickness in relation to walls forming the area around other portions of the surgical guide 100.

FIG. 3 also shows exemplary dimensions of the one or more slots 140 and one or more securement holes 150. As shown in this embodiment, the one or more slots 140 and the one or more securement holes 150 run through the front surface 135 and the conformal bone engaging surface 125. In various embodiments, the one or more slots 140 include a length 160, width 165, and depth 170. The length 160 and width 170 may vary depending on the specific patient case and use case (e.g., different resection techniques), but may generally be between 5 millimeters and 20 millimeters. In at least one embodiment, the depth 170 is between 5 millimeters to 50 millimeters, but this may be any suitable depth. In various embodiments, the securement holes 150 include a diameter 175 and depth 180. The diameter 170 may vary depending on the specific patient and use case, but may generally be between 3 and 15 millimeters. In at least one embodiment, the depth 180 is between 5 millimeters to 50 millimeters, but this may be any suitable depth.

As shown in this embodiment, the alignment holes 145 extend through a subset of certain walls 130 of the surgical guide 100, including, in this example, a first side wall 130A, second side wall 130B, and a middle wall 130C.

As shown in FIG. 3, the second end 110 includes one or more prongs 111, 112 that extend downwardly from the surgical guide 100. In at least one embodiment, the one or more prongs are angled away from the conformal bone engaging surface 125 to avoid certain anatomical structures (e.g., cartilage, bones such as the talus, etc.). The lengths and angled nature of the prongs 111, 112 may vary depending on patient anatomy. For example, the prongs 111, 112 may be of different lengths or the same length with respect to each other.

Figure 4:
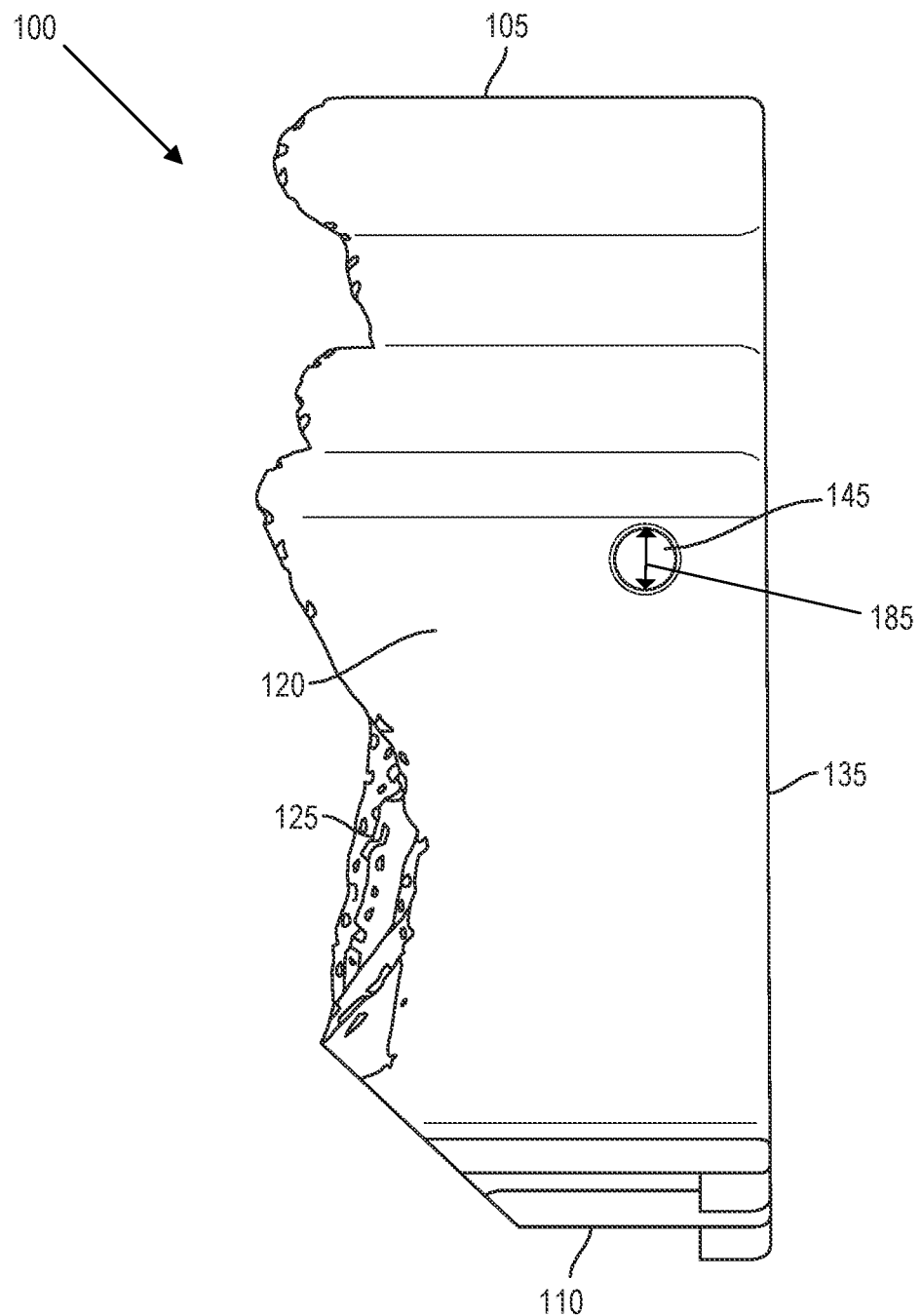
FIG. 4 is a side view of the exemplary tibial resection guide of FIG. 1, showing the guide mounted to a bone surface, according to one embodiment.

Turning now to FIG. 4, exemplary dimensions of the one or more alignment holes 145 are shown. In various embodiments, the one or more alignment holes 145 include a diameter 185 and depth 190 (seen in FIG. 3). The diameter 185 may vary depending on the specific patient case and use case, but may generally be between 2 and 15 millimeters. In at least one embodiment, the depth 190 is between 1 millimeter to 5 millimeters, corresponding with wall thickness 132, but this may be any suitable depth.

Figure 5:
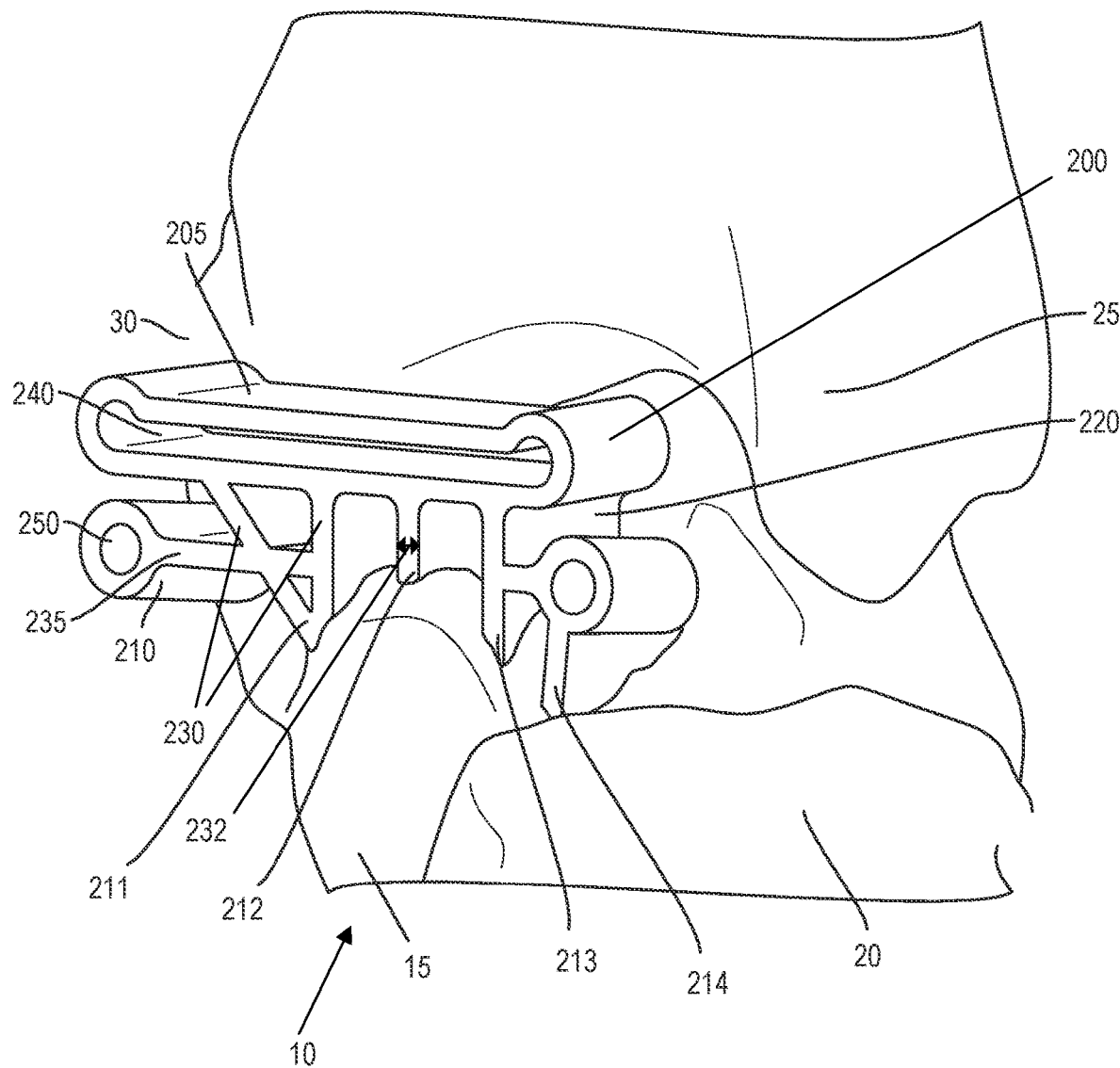
FIG. 5 is a perspective view of an exemplary talar resection guide, according to one embodiment.
Figure 6:
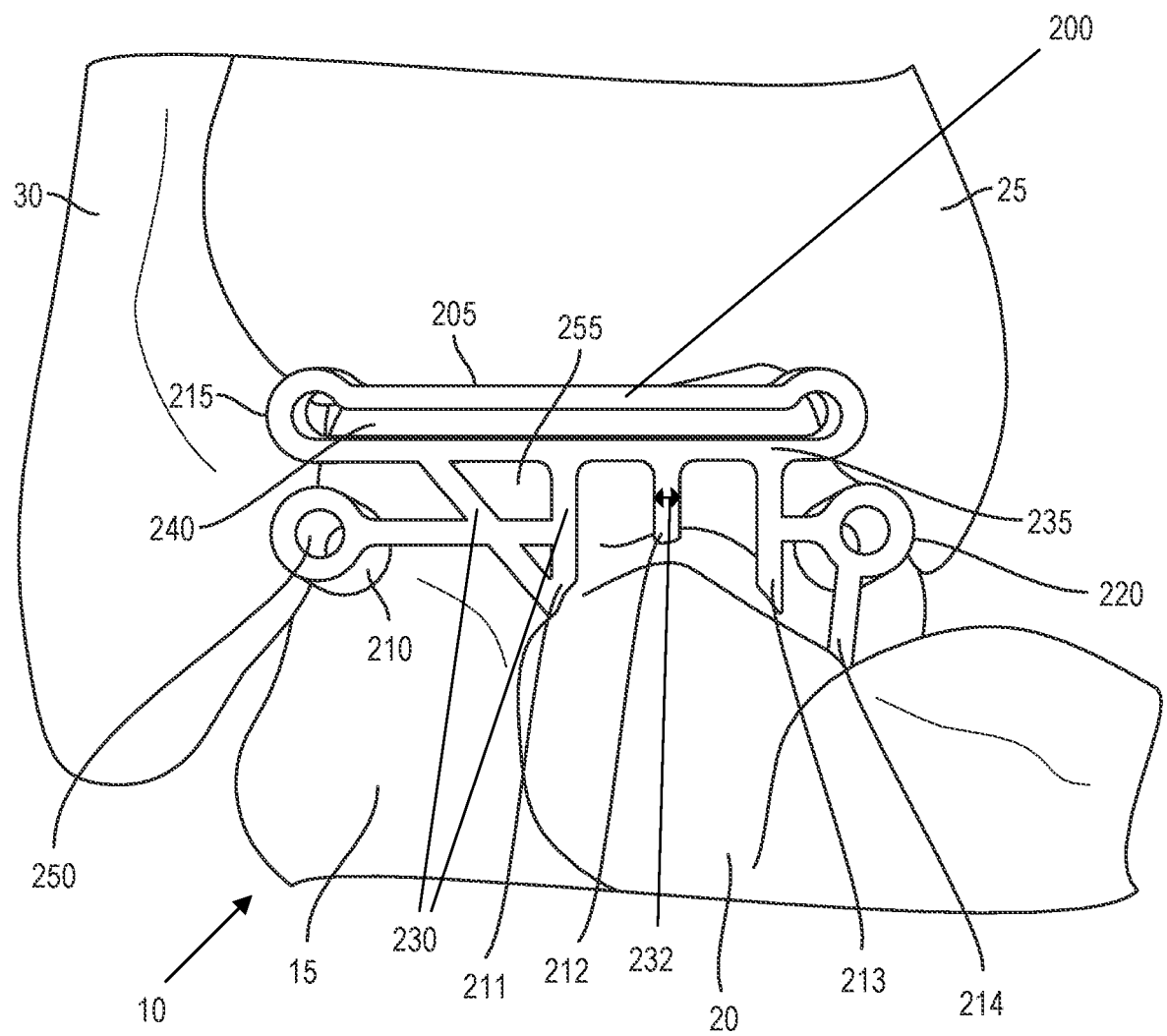
FIG. 6 is a front view of the exemplary talar resection guide of FIG. 5, showing the guide mounted to a bone surface, according to one embodiment.

Now referring to FIGS. 5 and 6, a surgical guide 200 is shown as an exemplary talar resection guide 200 bearing several similarities to the features of the exemplary tibial embodiments of FIGS. 1-4. In this embodiment, the surgical guide 200 is placed over a portion of the aforementioned patient ankle joint 10.

In the embodiment shown, the surgical guide includes a first end 205 and a second end 210, where the first end 205 is placed below a lowest surface of the tibia 25 and fibula 30 in contact with the talus 15, and the second end 210 is positioned above the calcaneus 20 in contact with the talus 15 such that the second end 210 avoids contact with patient cartilage. The surgical guide also includes a first side 215 and a second side 220, where the first side 215 is positioned toward a lateral side of the ankle joint 10 and the second side 220 is positioned toward a medial side of the ankle joint 10. As will be discussed with reference to FIG. 7, a conformal bone engaging surface 225 contacts the aforementioned bones of the ankle joint 10.

Figure 7:
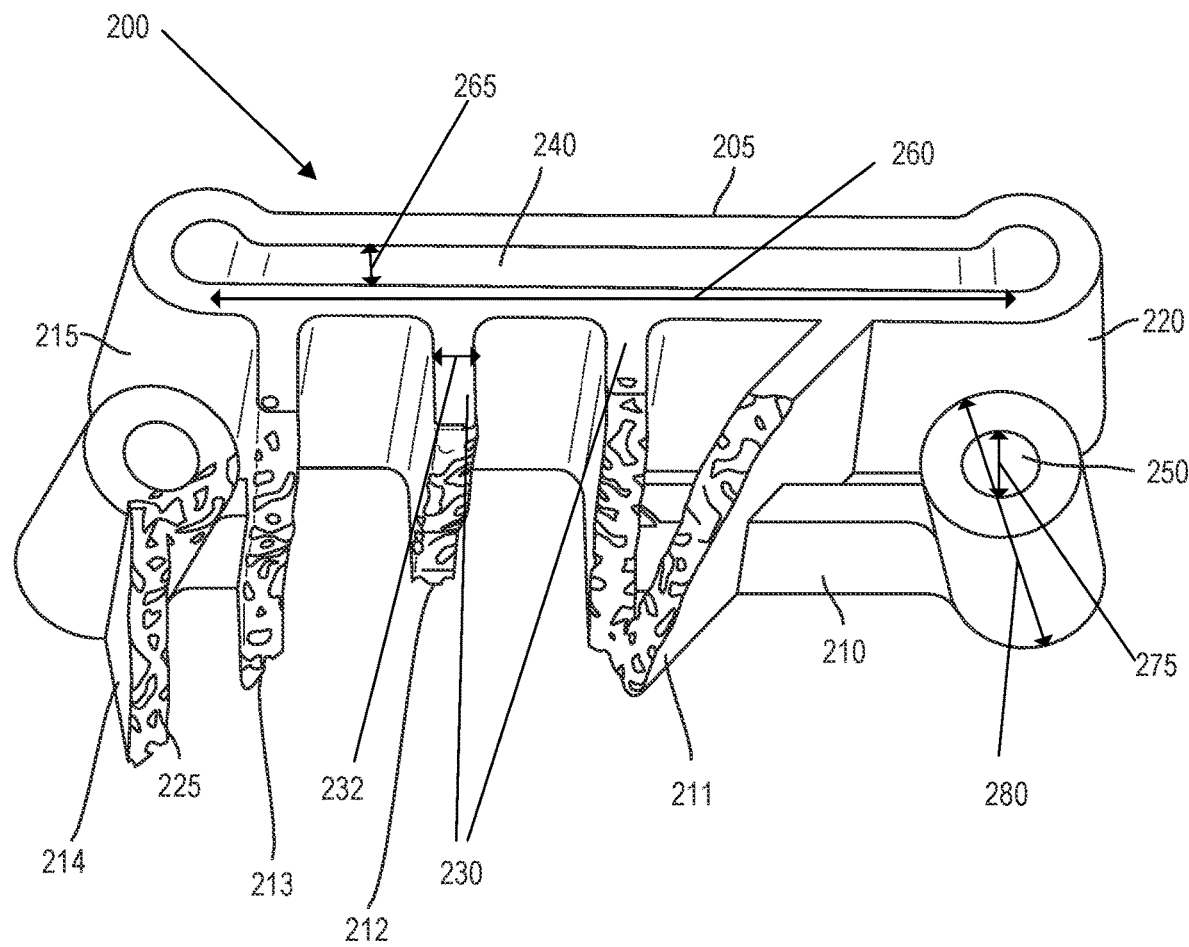
FIG. 7 is a perspective view of the exemplary talar resection guide of FIG. 5, showing the guide mounted to a bone surface, according to one embodiment.

In various embodiments, the second end 210 is at least partially patient-specific and may be pronged or otherwise constructed in order to contact the talus 15 and calcaneus 20 and avoid contact with soft tissues such as cartilage. As shown in FIG. 7, the second end 210 includes four prongs 211, 212, 213, 214 spaced at the medial and lateral sides of the talus 15. The prongs 211, 212, 213, 214 may aid in the positioning of the guide 100 over the talus 15 and calcaneus 20 such that the guide 200 is flush against the talus 15 and calcaneus 20, and avoids contact with soft tissues. In at least one embodiment, the prongs 211, 212, 213, 214 map to a specific surface of a patient's anatomy and are spaced to avoid cartilage, tendons, etc., but to provide support to the guide via contact with patient bone. In some embodiments, the spacing and contour of the prongs 211, 212, 213, 214 may allow for bone resection instrument articulation.

In alternate embodiments, there may be any suitable number of prongs or other support structures at any suitable spacing intervals on the second end 210 in accordance with the principles of this disclosure. In some embodiments, the portions of the prongs of the second end 210 that contact the talus 15 and calcaneus 20 may include one or more porous regions, thereby increasing the frictional fit between the talus 15 and calcaneus 20 and the overall guide 100. Further, the prongs 211, 212, 213, 214 of the second end 210 may contact the talus 15 and/or calcaneus 20 at an angle (shown in FIG. 7).

The surgical guide 200 may include one or more structural openings 255. The one or more structural openings 255 are located on a front surface 135 of the surgical guide 200, and extend through the body of the guide 200 and to a conformal bone engaging surface (shown in FIG. 7), forming one or more walls 230. The one or more structural openings 255 shown in FIGS. 5 and 6 are generally of a polygonal shape, but in other embodiments there may be any suitable number of structural openings 255, and they may be any suitable shape or size to form walls of any suitable shape, size, and/or thickness. The one or more structural openings 255 may aid in the structural integrity of the guide 200, reduce compositional material usage, or serve any other suitable purpose.

The surgical guide 200 may include a front surface 235 that may be generally flat or may be patient conforming. The front surface 235 may include one or more slots 240. The one or more slots 240 may have a length longer than its width, and extend through the body of the guide 100 to a conformal bone engaging surface (shown in FIG. 7). The one or more slots 240 may be situated on any portion of the front surface 235 without departing from the principles of this disclosure, generally wherever a user may find it beneficial to access and/or resect portions of the patient bone visible through the one or more slots 240. In at least one embodiment, the one or more slots 240 may be additionally beneficial for various resection techniques, allowing a user to use a wide variety of surgical equipment. As will be discussed with reference to FIG. 7, the one or more slots 240 may be at least partially defined by various dimensions including depth and length.

The front surface 235 may include one or more securement holes 250. The one or more securement holes 250 may have a circular or ovular shape, and extend through the guide 200 to a conformal bone engaging surface. The one or more securement holes 250 may be situated on any portion of the front surface 235 without departing from the principles of this disclosure, generally wherever a user may find it beneficial to secure the guide 200 to the patient bone. In at least one embodiment, the one or more securement holes 250 may be beneficial for securing the surgical guide 200 in place through use of equipment including, but not limited to, K-wires, nails, screws, or any other suitable attachment mechanism. As will be discussed with reference to FIG. 7, the one or more securement holes 250 may be at least partially defined by various dimensions including depth and length.

In various embodiments, the surgical guide 200 includes one or more walls 230, each of which may have a wall thickness 232 measuring between about 1.0-2.0 mm, or about 2.0-3.0 mm, or about 3.0-4.0 mm, or about 4.0-5.0 mm. Generally speaking, walls forming the area around the one or more securement holes 150 may vary in thickness in relation to walls forming the area around other portions of the surgical guide 200. Additionally, similar to the embodiments of FIGS. 1-4, alternative embodiments of the surgical guide 200 may include any number of suitable alignment holes (not pictured) which extend through a subset of the walls 230.

Turning now to FIG. 7, the conformal bone engaging surface 225 of surgical guide 200 is shown. In some embodiments, the conformal bone engaging surface 225 may exhibit a relatively rough texture in relation to other surfaces of the surgical guide 200. In other embodiments, the conformal bone engaging surface 225 is a porous surface and may optionally include a gyroid structure or any other suitable design without departing from the principles of this disclosure. In at least one embodiment, the porous surface is beneficial for keeping the surgical guide 200 in place during an orthopedic procedure (in case of guide 200 slippage) due to its texture, thus the conformal bone engaging surface 225 may exhibit a relatively high anisotropic resistance to various forces. The porous surface (and/or the entire guide) may be 3D printed in order to obtain a high degree of customizability in the surgical guide 200 for different patient applications.

FIG. 7 shows exemplary dimensions of the one or more slots 240 and one or more securement holes 250. As shown in this embodiment, the one or more slots 240 and one or more securement holes 250 run through the front surface 235 and out the conformal bone engaging surface 225. In various embodiments, the one or more slots 240 include a length 260, width 265, and depth 270. The length 260 and width 270 may vary depending on the specific patient case and use case (e.g., different resection techniques), but may generally be between 5 millimeters and 20 millimeters. In at least one embodiment, the depth 270 is between 5 millimeters to 50 millimeters, but may be any suitable depth. In various embodiments, the securement 250 include a diameter 275 and depth 280. The diameter 270 may vary depending on the specific patient case and use case, but may generally be between 3 and 15 millimeters. In at least one embodiment, the depth 280 is between 5 millimeters to 50 millimeters, but this may be any suitable depth.

Figure 8:
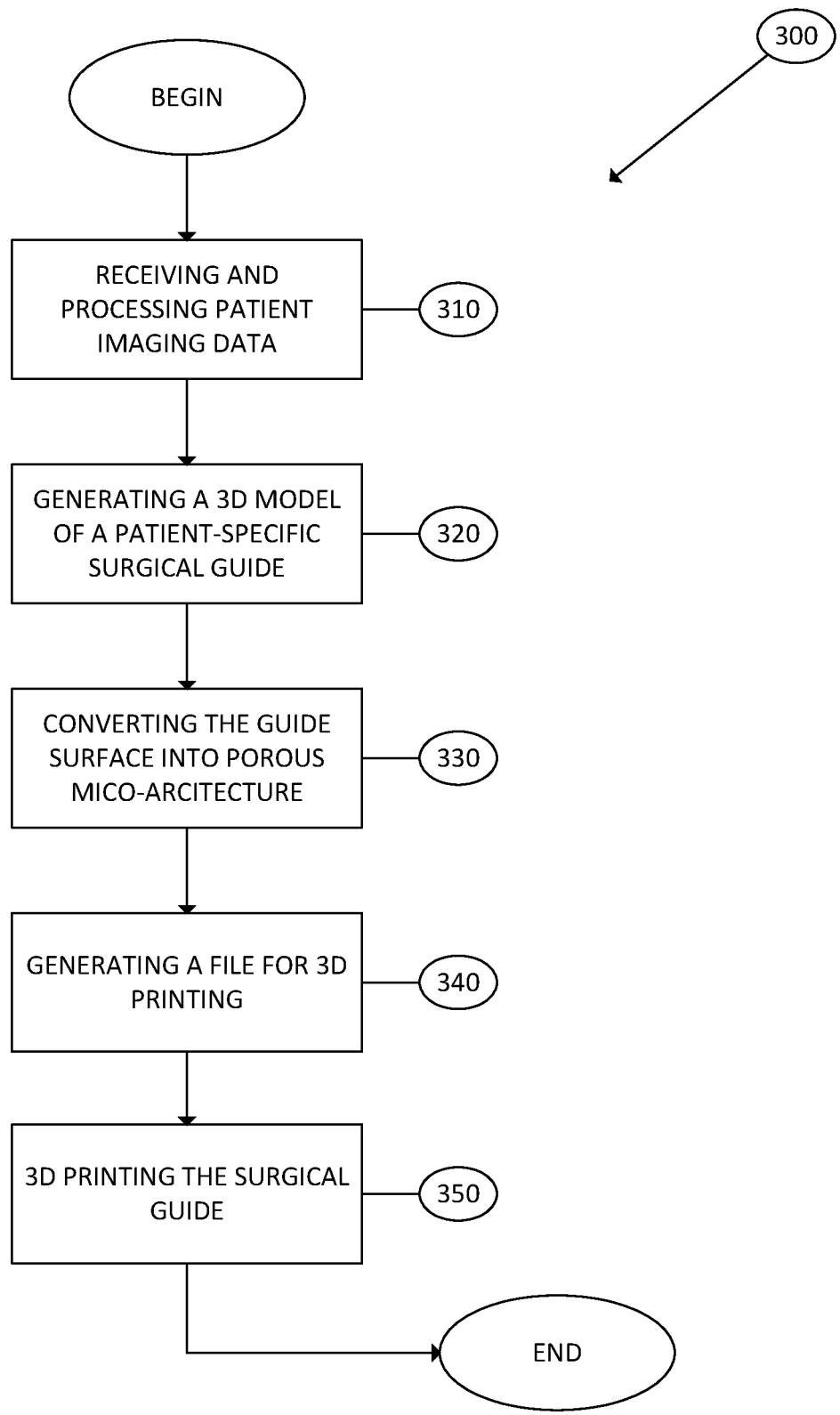
FIG. 8 is a flow chart of an exemplary surgical guide manufacturing process, according to one embodiment.

Referring now to FIG. 8, in at least one embodiment, the surgical guide structures are produced by 3D printing manufacturing methods. As will be understood from discussions herein, the exemplary guides that include patient-specific and porous structures may be produced via additive manufacturing (e.g., 3D printing) techniques that produce the entirety of the guides on a layer-by-layer basis. In other words, in at least some embodiments, the guides discussed herein have integrally formed porous surfaces that are created with the rest of the surgical guide (e.g., a porous surface is not added via post-processing). In other embodiments, guides discussed herein may include porosity added via post-processing.

The process 300 generally starts with step 310, receiving and processing patient imaging data. In various embodiments, the patient imaging data can be one or more DICOM files, series of 2D images, or any other type of suitable imaging data. This includes imaging data from anywhere in the body, such as the hands, feet, shoulders, knees, elbows, face, head, arms, legs, hips, pelvis, spine, back, etc.

Based on the received patient imaging data, at step 320, the system generates a 3D model of a patient-specific surgical guide based on received patient imaging data. In various embodiments, the 3D model may be produced based on a 3D model of patient anatomy (also produced by the system) or might be based on previously produced guides. As discussed herein, the patient-specific surgical guide may include at least one patient-specific surface.

At step 330, the system converts at least a portion of the patient-specific surface into a porous micro-architecture. As discussed herein, the porous micro-architecture may be defined as including porous and/or gyroid structures. The porous micro-architecture may cover the entire patient-specific surface, some portions of the patent-specific surface, or certain percentages (such as 15-85%) of the patient-specific surface. As also discussed herein, the porous micro-architecture may be designed or created automatically by the system based on the received patient data (e.g., the system automatically adds a porous surface to the patient specific surface and adjusts the porous surface for a specific depth (e.g., based on aspect ratio or the like), length, size, area, etc.). The surgical guide may also include macro-architecture features, such as pins, nails, etc.

At step 340, the system generates a file for 3D-printing the patient-specific surgical guide based on the 3D model. In various embodiments, the system automatically combines the surface created at step 330 and the guide model produced at steps 320 to create a file readable by a 3D printer or like machine. In some embodiments the surface created at step 330 and the guide model produced at step 320 are produced together and modified to be read by a 3D-printer or like system.

At step 350, the system prints the patient-specific surgical guide including the patient-specific surface with the porous micro-architecture 350.

Figure 9:
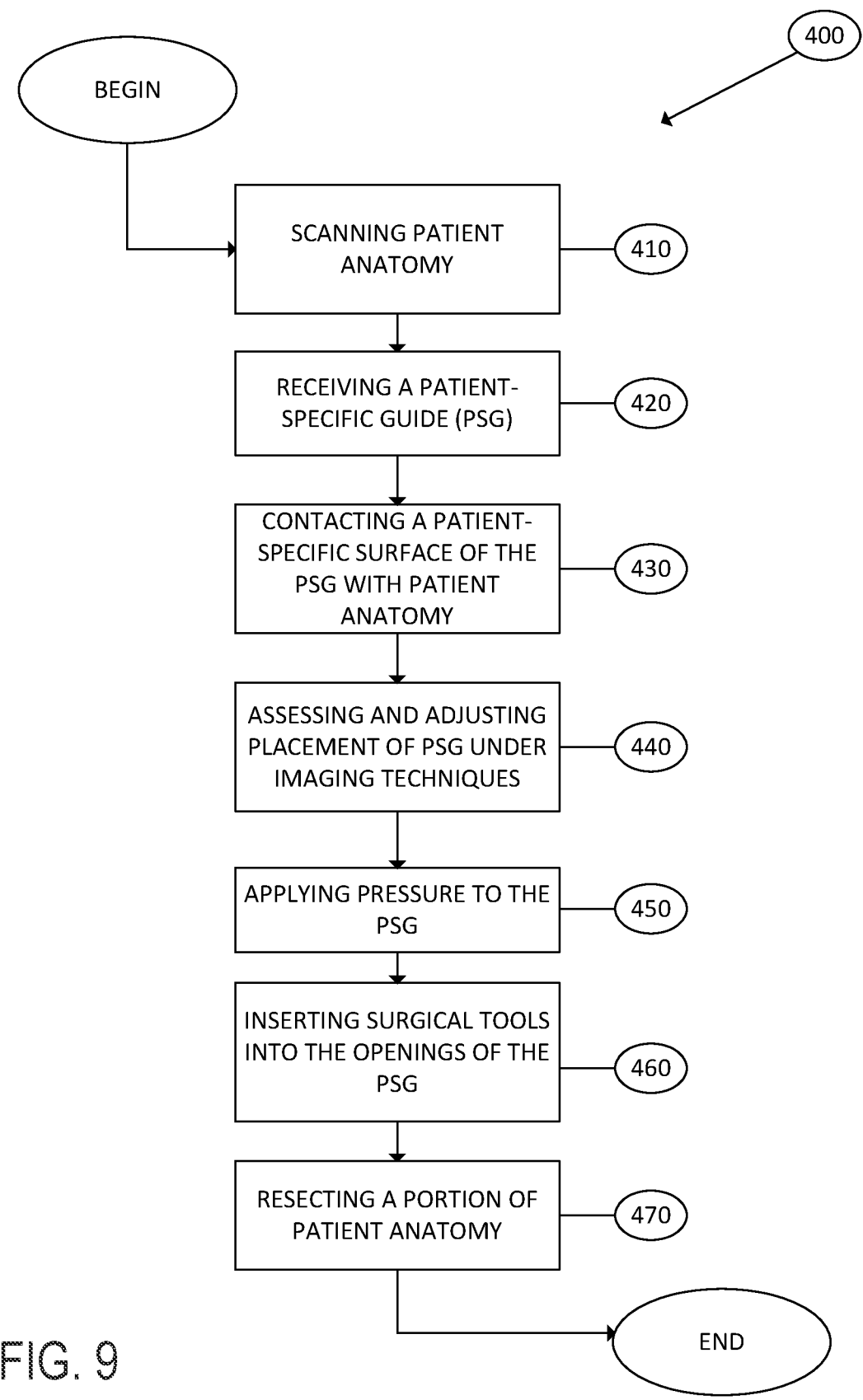
FIG. 9 is a flow chart of an exemplary surgical process, according to one embodiment.

FIG. 9 describes a method 400 of using the surgical guide. The method 400 may generally include any of the above steps described in regard to FIG. 8, including, but not limited to scanning patient anatomy at step 410.

As shown in FIG. 9, a user (e.g., surgeon), receives a patient-specific surgical guide including a patient-specific surface, the patient-specific surface including a porous micro-architecture at step 420. As will be understood, the patient-specific surgical guide may include additional other instruments, guides, implants, or the like packaged with the guide or separately.

At step 430, the user intraoperatively contacts the patient-specific surface with patient anatomy, which includes the porous micro-architecture, with the patient anatomy in order press into soft tissues present on a bone surface.

At step 440, the user assesses and adjusts placement of the patient-specific guide under imaging techniques (e.g., CT scanning, standing x-rays). As discussed with regarding FIGS. 1-7, certain features of the patient-specific guide (e.g., one or more slots, one or more securement holes, one or more alignment holes, one or more structural openings) enable a user to adjust the positioning of the guide, such as the alignment and securement holes.

Once the user has positioned the patient-specific guide, the user applies pressure to the surgical guide such that the guide is sufficiently secured onto the patient anatomy at step 450. As discussed above, a depth of the porosity of the guide may account for a depth of any periosteum (plus an additional factor). In various embodiments, a user may exert force and "press" the patient-specific guide onto the patient anatomy in order to pierce through any periosteum present on a bone surface to contact the guide directly with the bony surface (or otherwise ensure the secure positioning of the guide on the patient anatomy).

At step 460, the user inserts surgical instruments through the plurality of openings.

As discussed herein, embodiments of the patient-specific guide are constructed from metals (e.g., titanium) as opposed to plastics, additional metal jigs may not be needed for the accurate positioning of the patient-specific guide on patient anatomy. This is due to the porous texture of the conformal bone engaging surface increasing the anisotropic frictional force between the guide and patient anatomy, the material composition allowing the guide to appear under medical imaging techniques, and because surgical tools may not be able to cut through metal.

At step 470, the user resects a portion of the patient anatomy based on the placement of the patient-specific surgical guide. As will be understood, a user may resect patient anatomy along slots, openings, and/or holes in the patient-specific surgical guide.

Exemplary processes for producing one of more implants corresponding to the patient-specific surgical guides can be found in the following patent and patent application incorporated herein by reference as if set forth in their entireties:

U.S. Pat. No. 11,026,798, issued on Jun. 8, 2021, and entitled SHEET BASED TRIPLY PERIODIC MINIMAL SURFACE IMPLANTS FOR PROMOTING OSSEOINTEGRATION AND METHODS FOR PRODUCING SAME; and U.S. patent application Ser. No. 17/314,378, filed on May 7, 2021, and entitled SPATIALLY VARIED IMPLANTS AND PROCESSES FOR MAKING AND USING SAME.

ALTERNATE EMBODIMENTS

It is understood that the present disclosure is highly customizable, and any type of surgical guide can be configured with any number and placement of slots, holes, additional recesses, and/or material textures of any shape and size to attach onto any type of bones. Additionally, while the embodiments shown herein may include various walls and openings that result in partially polygonal, angular, convex, concave, or otherwise suitable shapes of the surgical guide, other embodiments may be entirely patient-specific such that the guide encompasses an organic shape of varying thicknesses (e.g., without walls and/or hard angles and comprising minimal material). Furthermore, additional embodiments may be configured for use in various applications including, but not limited to, craniomaxillofacial surgical procedures involving the mandible, maxilla, and/or cranium.

The surgical guides discussed herein may include features to guide the depth of a cut by a surgical tool. For example, the guide may include a first "as-manufactured" instrument, the depth of which may be modified to interface with surgical tools such as a predetermined saw, drill, burr, or other assembly that may have an interfacing surface that "bottoms out" on the as-manufactured instrument. As described herein, "as-manufactured" may be construed to mean 3D printed or 3D printed and post-processed (which may further include material removal). In additional embodiments, any suitable second instrument may be coupled to the as-manufactured guide and may include a surface onto which the surgical tool may bottom out. In either case, the surface that the surgical tool bottoms out onto can be flat, angled, curvilinear, stepped, faceted, or other otherwise modified as per patient-specific attributes. In other embodiments, a third instrument may be coupled to the surgical tool that may include a flat, angled, curvilinear, stepped, faceted, or otherwise modified surface as per patient-specific attributes. The third instrument may bottom out onto either the as-manufactured guide or the second instrument coupled to the guide.

The surgical guides discussed herein may include additional visual and/or fluoroscopic features indicating depth, length, and/or angular measurement markings, or any other markings positioned at predetermined intervals. The markings may correlate with specific patient anatomy and may assist a user in performing surgical procedures and/or orientating the guide relative to the patient's anatomy.

Furthermore, the surgical guides discussed herein may be used in applications involving augmented reality (AR), where digital superimposition of virtual objects (e.g., CT scan of patient anatomy) onto physical objects (e.g., patient anatomy) or within space may aid the preoperative planning, surgical execution, and post operations of orthopedic procedures. In some embodiments, an optical tracking system may be applied to the surgical guides such that features of predetermined size (e.g., a section of a sphere) may be identified. Attachment points (e.g., threaded attachment holes) on the surgical guides may accept the placement of an optical tracking sensor detectable by the optical tracking system. The surgical guides may also be equipped with additional sensors connected to an AR and/or IoT system that assist with data preparation and recording, visualization, and registration/tracking, thereby improving information transfer and consideration during surgery, and offering opportunities for continuous learning.

For example, with reference to the embodiment of FIG. 1, the one or more securement holes 150, one or more alignment holes 145, and/or one or more slots 140 may be equipped with sensors that aid in optical tracking and data recordation. In connection with an AR and/or IoT system, the captured information may be interfaced with surgical tools that aid in correctly positioning the guide 100 over patient anatomy. AR and IoT capabilities may also streamline orthopedic procedures by controlling or partially controlling the operation of surgical tools (e.g., saw blades, drills), thereby yielding higher accuracy in surgical execution, reduction of radiation exposure, and decreased surgery time and mistakes.

The invention claimed is:

1. A patient-specific surgical guide comprising:
   a 3D-printed body comprising:
   a metallic material;
   a front surface;
   a conformal bone engaging surface opposite the front surface and contoured to a patient's anatomy, the conformal bone engaging surface comprising one or more gyroid structure regions; and
   a plurality of openings extending through the 3D-printed body between the conformal bone engaging surface and the front surface, wherein:
   at least one of the plurality of openings is sized to receive a surgical instrument for resecting a portion of the patient's anatomy; and
   the one or more gyroid structure regions comprise: i) an average pore depth of 0.2 mm to 2.0 mm; and ii) a minimum feature size of 0.1 mm to 2 mm.

2. The patient-specific surgical guide of claim 1, wherein at least one of the gyroid structure regions has an effective radius of 0.5 mm to 1 mm.

3. The patient-specific surgical guide of claim 2, wherein:
   the 3D-printed body comprises one or more walls; and
   at least one of the plurality of openings extends through the one or more walls.

4. The patient-specific surgical guide of claim 3, wherein:
   the 3D-printed body comprises a first end, a second end, a first side, and a second side; and
   the first end, the second end, the first side, and the second side are contoured to avoid at least one soft tissue structure of the patient's anatomy.

5. The patient-specific surgical guide of claim 4, wherein the at least one of the plurality of openings is an elongate slot.

6. The patient-specific surgical guide of claim 5, wherein the surgical instrument comprises a saw blade.

7. The patient-specific surgical guide of claim 6, wherein one or more of the plurality of openings is a structural opening.

8. The patient-specific surgical guide of claim 6, wherein one or more of the plurality of openings is a securement hole.

9. The patient-specific surgical guide of claim 6, wherein one or more of the plurality of openings is an alignment hole.

10. A patient-specific surgical guide comprising:
    a 3D-printed body comprising:
    a rigid material;
    a front surface;
    a conformal bone engaging surface opposite the front surface and contoured to a patient's anatomy, the conformal bone engaging surface comprising one or more porous regions; and
    a plurality of openings extending through the 3D-printed body between the conformal bone engaging surface and the front surface, wherein:
    at least one of the plurality of openings is sized to receive a surgical instrument for resecting a portion of the patient's anatomy; and
    the one or more porous regions comprise an average pore depth of 0.2 mm to 2.0 mm.

11. The patient-specific surgical guide of claim 10, wherein:
    the 3D-printed body comprises a first end, a second end, a first side, and a second side; and
    the first end, the second end, the first side, and the second side are contoured to avoid at least one soft tissue structure of the patient's anatomy.

12. The patient-specific surgical guide of claim 11, wherein at least one of the one or more porous regions has an effective radius of 0.5 mm to 1 mm.

13. The patient-specific surgical guide of claim 12, wherein at least one of the one or more porous regions has a minimum feature size of 0.1 mm to 2 mm.

14. The patient-specific surgical guide of claim 13, wherein the one or more porous regions comprise a gyroid structure.

15. The patient-specific surgical guide claim 14, wherein the rigid material comprises a metallic material.

16. The patient-specific surgical guide of claim 15, wherein the at least one opening of the plurality of openings is an elongate slot.

17. The patient-specific surgical guide of claim 16, wherein one or more of the plurality of openings is a structural opening.

18. The patient-specific surgical guide of claim 16, wherein one or more of the plurality of openings is a securement hole.

19. The patient-specific surgical guide of claim 16, wherein one or more of the plurality of openings is an alignment hole.

20. A method for using a patient-specific surgical guide, the method comprising:
  receiving a 3D-printed patient-specific surgical guide, the patient-specific surgical guide comprising:
    a rigid material;
    a front surface;
    a conformal bone engaging surface opposite the front surface and contoured to patient anatomy, the conformal bone engaging surface comprising one or more porous regions;
    the one or more porous regions comprising:
      an average pore depth of 0.2 mm to 2.0 mm; and
      a minimum feature size of 0.1 mm to 2 mm;
    a plurality of openings extending through the 3D-printed patient-specific surgical guide between the conformal bone engaging surface and the front surface and sized to receive a surgical instrument for resecting a portion of the patient anatomy;
  intraoperatively engaging the conformal bone engaging surface with the patient anatomy;
  inserting the surgical instrument through an elongate slot; and
  resecting a portion of the patient anatomy based on the placement of the patient-specific surgical guide.

21. The method of claim 20 further comprising the step of pressing at least one of the one or more porous regions of the patient-specific surgical guide onto soft tissues surrounding the patient anatomy.

* * * * *